(12) United States Patent
Gu et al.

(10) Patent No.: US 7,019,309 B2
(45) Date of Patent: Mar. 28, 2006

(54) TRIPARTITE FIBER-COUPLED FLUORESCENCE INSTRUMENT

(75) Inventors: Min Gu, Doncaster (AU); Damian Bird, Hawthorn (AU)

(73) Assignee: Swinburne University of Technology, Victoria (AU)

( * ) Notice: Subject to any disclaimer, the term of this patent is extended or adjusted under 35 U.S.C. 154(b) by 300 days.

(21) Appl. No.: 10/460,188

(22) Filed: Jun. 13, 2003

(65) Prior Publication Data

US 2004/0061072 A1 Apr. 1, 2004

(30) Foreign Application Priority Data

Sep. 30, 2002 (AU) .............................. 2002951841

(51) Int. Cl.
G01N 21/64 (2006.01)
(52) U.S. Cl. .................................................. 250/458.1
(58) Field of Classification Search ................ 600/160, 600/317; 250/458.1
See application file for complete search history.

(56) References Cited

U.S. PATENT DOCUMENTS

| | | | | |
|---|---|---|---|---|
| 4,447,119 A | * | 5/1984 | Beasley ...................... | 385/137 |
| 4,904,085 A | * | 2/1990 | Spillman Jr. et al. ....... | 356/364 |
| 5,239,998 A | * | 8/1993 | Krauthamer ................ | 600/317 |
| 5,593,406 A | * | 1/1997 | Eggers et al. ................ | 606/29 |
| 5,865,729 A | * | 2/1999 | Meehan et al. ............. | 600/207 |
| 6,369,928 B1 | | 4/2002 | Mandella et al. | |
| 6,485,413 B1 | * | 11/2002 | Boppart et al. ............. | 600/160 |
| 2003/0031410 A1 | * | 2/2003 | Schnitzer ..................... | 385/34 |
| 2004/0126694 A1 | * | 7/2004 | Devoe et al. ............. | 430/270.1 |

FOREIGN PATENT DOCUMENTS

| | | |
|---|---|---|
| GB | 2 338 568 A | 12/1999 |
| GB | 2 341 943 A | 3/2000 |
| GB | 2 353 369 A | 2/2001 |
| WO | WO 01/59423 A2 | 8/2001 |
| WO | WO 02/064084 A2 | 8/2002 |

OTHER PUBLICATIONS

Winfried Denk, James H. Strickler, Watt W. Webb, Two-Photon Laser Scanning Fluorescense Microscopy, Science, Apr. 6,1990, 248, 4951, pp. 73-76.

(Continued)

Primary Examiner—David Porta
Assistant Examiner—Mindy Vu
(74) Attorney, Agent, or Firm—Sughrue Mion, PLLC

(57) ABSTRACT

A non-linear fluorescence microscope or endoscope includes: (a) a source of coherent light suitable to initiate non-linear fluorescence in a sample of interest located at a sample region; (b) a first light conductor positioned to receive at its terminal light from the light source and direct the light to a coupler; (c) a second light conductor located to receive light introduced to the coupler from the first conductor and direct the light to the sample via a sample end of the second conductor, the sample end also located to receive fluoresced light from the sample such that the second conductor may direct the fluoresced light to the coupler; and (d) a third light conductor located to direct fluoresced light from the coupler to a light detection device via a terminal of the third light conductor.

17 Claims, 11 Drawing Sheets

OTHER PUBLICATIONS

Tim Dabbs and Monty-Glass, Fiber-optic confocal microscope: FOCAN, Applied Optics, vol. 31, No. 16, Jun. 1, 1992; pp. 3030-3035.

Jos Benschop and Gerard Van Rosmalen, Confocal compact scanning optical microscope based on compact disc technology, Applied Optics, vol. 30, No. 10, Apr. 1, 1991; pp. 1179-1184.

Shigeharu Kimura and Tony Wilson, Confocal scanning optical microscope using single-mode fiber for signal detection, Applied Optics, vol. 30, No. 16; Jun. 1 1991; pp. 2143-2150.

Min Gu, C.J.R. Sheppard, and X. Gan, Image formatin in a fiber-optical confocal scanning microscope, Optical Society of America, vol. 8, No. 11, Nov. 11, 1991; pp. 1755-1761.

Damian Bird and Min Gu, Resolution improvement in two-photon fluorescence microscopy with a single-mode fiber, Applied Optics, vol. 41, No. 10, Apr. 1, 2002; pp. 1852-1857.

M. Vaez Iravani, Fibre-optic scanning differential interference contrast optical microscope, Electronics Letters, vol. 22, No. 2, Jan. 16,1986; pp. 103-105.

Y. Fujii and Y. Yamazaki, A fibre-optic 3-D microscope with high depth sensitivity, Journal of Microscopy; vol. 158, Pt. 2, May 1990; pp. 145-151.

H. Zhou, C.J.R. Sheppard and M. Gu; A compact confocal interference microscope based on a four-port single-mode fibre coupler, Optick, 103, No. 1 (1996, pp. 45-48.

G.J. Tearney, S.A.Boppart, B.E. Bouma, M.E. Brezinski, N.J. Weissman, J.F. Southern, and J.G. Fujimoto, Scanning single-mode fiber optic catheter-endoscope for optical coherence tomography, Optics Letters, vol. 21, No. 7, Apr. 1, 1966, pp. 543-545.

Francois Ouellette, All-fiber for efficient dispersion compensation, Optics Letters, vol. 16, No. 5, Mar. 1, 1991; pp. 303-305.

Benjamin J. Eggleton, Peter A. Krug, L. Poladian, K.A. Ahmed, and H.F. Liu, Experimental demonstration of compression of dispersed optical pulses by reflection from self-chirped optical fiber Bragg gratings, Optics Letters, vol. 19, No. 12, Jun. 15, 1994, pp. 877-879.

M.E. Fermann, K. Sugden, and I. Bennion, Environmental stable high-power soliton fiber lasers that use chirped fiber Bragg gratings, Optics Letters, vol. 20, No. 15, Aug. 1, 1995, pp. 1625-1627.

Damian Bird and Min Gu, Compact two-photon fluorescense microscope based on a single-mode coupler, Optics Letters, vol. 27, No. 12, Jun. 15, 2002; pp. 1031-1033.

* cited by examiner (a)

(b)

TRIPARTITE FIBER-COUPLED FLUORESCENCE INSTRUMENT

FIELD OF THE INVENTION

The present invention relates to a non-linear fluorescence, particularly two-photon fluorescence, microscope or endoscope, including an endomicroscope. The invention also relates to components of such apparatus and to processes for microscopy, endoscopy and/or endomicroscopy.

BACKGROUND OF THE INVENTION

Since its inception[1] non-linear fluorescence microscopy (that is, where for a given power input there is non-linear fluorescence intensity), particularly two-photon fluorescence microscopy, has rapidly emerged as an important technique for three-dimensional imaging of biological specimens, and in particular for use in surgical biopsy and early cancer detection. For example in relation to two-photon fluorescence microscopy this rapid emergence can be attributed to advantages offered by two-photon excitation relative to single-photon excitation. These advantages include an inherent optical sectioning property, confinement of photo damage to the focal region and improved depth penetration into a sample[1]. The feature of confinement arises as two-photon induced absorption is most probable in the focal volume where the photon energy density is highest. In fact, the out-of-focus fluorophores are safeguarded from photobleaching since the energy density is not sufficient to induce fluorescence at these points. The third-order nonlinear excitation probability makes it possible to image a single point of the specimen, preserving the fluorophores at other axial depths for subsequent observation. The ability to discriminate against fluorescence originating from outside of the focal spot is a powerful property of the imaging modality that provides an inherent optical sectioning effect for the acquisition and reconstruction of 3-D images.

However, one of the greatest restrictions to the development of two-photon microscopy particularly in relation to in vivo applications, is that the known apparatus require the use of complicated pulse lasers and bulk optics. While the introduction of optical fibers and fiber components to coherent (single-photon) fluorescence imaging systems[2-5] has overcome some physical limitations, and offered an ability to image specimens in vivo by delivering excitation radiation to a remote sample, the present single-photon arrangements remain bulky, cumbersome to operate, expensive and limited in their functionality. In addition to these problems the application of fiber optics to two-photon fluorescence systems has been hindered by the perceived problem of dispersion of the short pulses required for two-photon fluorescence. The present inventors have now devised apparatus that may address or at least obviate to some extent a number of the problems outlined above.

In one aspect of the present invention the microscope or endoscope comprises single-mode fiber for delivery of an ultra short pulsed laser beam, and a multi-port fiber coupler replaces bulk optics for illumination delivery and signal collection. Although a multi-port fiber coupler has been used in scanning differential interference contrast microscopy[7], confocal reflection microscopy[2,8] and confocal interference microscopy[9], such arrangements have not successfully been adopted in relation to two-photon fluorescence microscopy or endoscopy. It was previously thought impractical to adopt such an arrangement due to the fact that the separation of the excitation and fluorescence wavelengths is so large that the fiber coupler would be unable to efficiently transmit light at these distinct wavelengths. However, the present inventors have found that it is possible in the present apparatus for the excitation and fluorescence wavelengths to be transmitted with satisfactory efficiency.

A further advantageous aspect of the present invention is that it exhibits a self-aligning nature, because the illumination delivery and signal collection beams utilise the same port. In embodiments of the invention that utilise a small fiber aperture, image resolution of the new system may be significantly improved, and multiple scattering may be reduced, relative to conventional two-photon fluorescence endoscopes or microscopes (as for example described in UK patent applications 2,353,369 and 2,341,943).

UK patent number 2,338,568 discloses an endoscope/microscope apparatus where the laser light pulses are split by a beam splitter and are reflected back towards the beam splitter by anti-dispersive gratings in order to condense the light pulses. Within this document there is insufficient information provided to demonstrate effectiveness of the arrangement, which is not considered likely to be particularly suitable for use in two-photon fluorescence endoscopic applications due to component bulk and space separation between the dispersing means and sample.

In another aspect the present invention utilises a scanning head for delivery of illuminating light to the sample and for signal collection from the sample. Although a similar approach has previously been used for acquisition of optical coherence tomography (OCT) images of in vitro human saphenous vein[10] it was previously considered that this type of micro-scanning head would result in unacceptable levels of temporal dispersion at the increased powers required for non-linear (especially two-photon) fluorescence, compared to those adopted in OTC.

SUMMARY OF THE INVENTION

According to one embodiment of the present invention there is provided a non-linear fluorescence microscope or endoscope comprising:

(a) a source of coherent light suitable to initiate non-linear fluorescence in a sample of interest to be located at a sample region;

(b) a first light conductor positioned to receive at its terminal light from said light source and direct said light to a coupler;

(c) a second light conductor located to receive light introduced to said coupler from said first conductor and direct said light to said sample via a sample end of said second conductor, said sample end also located to receive fluoresced light from said sample such that said second conductor may direct said fluoresced light to said coupler;

(d) a third light conductor located to direct fluoresced light from said coupler to a light detection device via a terminal of said third light conductor.

The non-linear fluorescence is preferably two-photon fluorescence.

Preferably the light conductors comprise optic fiber. It is preferred that the coupler is a three-port single-mode fiber coupler.

In another preferred aspect a neutral density filter is provided, rotation of which allows power variation of the coherent light. Preferably the neutral density filter is located such that light emanating from the source of coherent light passes through it directly from the source. A lens is preferably provided to direct coherent light from the source to the terminal of the first conductor.

It is also preferred that a fiber chuck is located at the terminal of the first light conductor. The position of the fiber chuck located at the terminal of the first light conductor may be controlled by a positioning device.

Preferably a first lens is provided to collimate light emanating from the sample end toward the sample. A second lens is preferably provided to collect said fluoresced light from said sample and a variable aperture is preferably provided between said first lens and said second lens. Preferably the first lens, the second lens, the variable aperture and the sample end are contained within a protective housing.

A fiber chuck is preferably located at the sample end of the second conductor. The fiber chuck located at the sample end may be controlled by a positioning device.

Preferably a filter is provided between the detection device and the terminal of the third light conductor which substantially prevents passage to the detection device of light other than the fluoresced light. Preferably this filter is a bandpass filter. A fiber chuck is preferably located at the terminal of the third light conductor. The position of the fiber chuck located at the terminal of the third light conductor may be controlled by a positioning device.

In a preferred embodiment of the invention the detection device is a photomultiplier tube.

It is preferred that the source of coherent light is a pulse laser. Preferably the laser is a Ti:Sapphire laser. Preferably the coherent light is at a wavelength of between about 730 nm to about 870 nm.

In the case of an endoscope a suction mechanism for drawing the sample into the sample region is optionally provided. A camera and light source to assist in directing the sample region to a desired location may also be provided. Also in the case of an endoscope a heater for heating some or all components of the endoscope located internally during use of the endoscope, may be provided.

In a further preferred embodiment there is provided a scanning head at said sample end. The scanning head may comprise a gradient index lens located to receive light from said sample end, and an optical prism which directs light from said gradient index lens transverse to axis of said gradient index lens. Preferably the optical prism directs light in a substantially perpendicular direction from said axis.

In another embodiment of the present invention there is provided a two-photon fluorescence microscope or endoscope comprising:

(a) a source of coherent light suitable to initiate two-photon fluorescence in a sample of interest to be located at a sample region;

(b) a first fiber optic light conductor having at its terminal a fiber chuck under positional control of a positioning device, wherein light from said source passes through a neutral density filter and a lens which directs the light to the terminal of the first conductor, which in turn directs said light to a three-port single mode fiber coupler;

(c) a second fiber optic light conductor having at its sample end a fiber chuck under positional control of a positioning device, the second conductor located to receive light from said first conductor and direct light to said sample via the sample end from which a first lens collimates light emanating from said sample end, which light is then directed to said sample through a variable aperture and a second lens, said sample end also located to receive fluoresced light from said sample that is collected by said second lens, passes through said aperture and is directed to said sample end by said first lens;

(d) a third fiber optic light conductor having at its terminal a fiber chuck under positional control of a positioning device, the third conductor located to direct light from said coupler to a photormultiplier tube light detection device via said terminal of said third conductor and a bandwidth filter that substantially prevents passage to said detection device of light other than said fluoresced light.

In another embodiment of the present invention there is provided a two-photon fluorescence endomicroscope comprising:

(a) a source of coherent light suitable to initiate two-photon fluorescence in a sample of interest to be located at a sample region;

(b) a first fiber optic light conductor having at its terminal a fiber chuck under positional control of a positioning device, wherein light from said source passes through a neutral density filter and a lens which directs the light to the terminal of the first conductor, which in turn directs said light to a three-port single mode fiber coupler;

(c) a second fiber optic light conductor having at its sample end a scanning head comprising a gradient index lens located to receive light from said sample end, and an optical prism which directs light from said gradient index lens transverse to axis of said gradient index lens, the second conductor located to receive light from said first conductor and direct light to said sample via the sample end, said sample end also located to receive fluoresced light from said sample that is collected by said optical prism, passes through said gradient index lens and is thereby directed to said sample end;

(d) a third fiber optic light conductor having at its terminal a fiber chuck under positional control of a positioning device, the third conductor located to direct light from said coupler to a photomultiplier tube light detection device via said terminal of said third conductor and a bandwidth filter that substantially prevents passage to said detection device of light other than said fluoresced light.

BRIEF DESCRIPTION OF THE FIGURES

The present invention will be further described by way of example only with reference to the following figures, wherein.

DETAILED DESCRIPTION OF THE INVENTION

Figure 1:
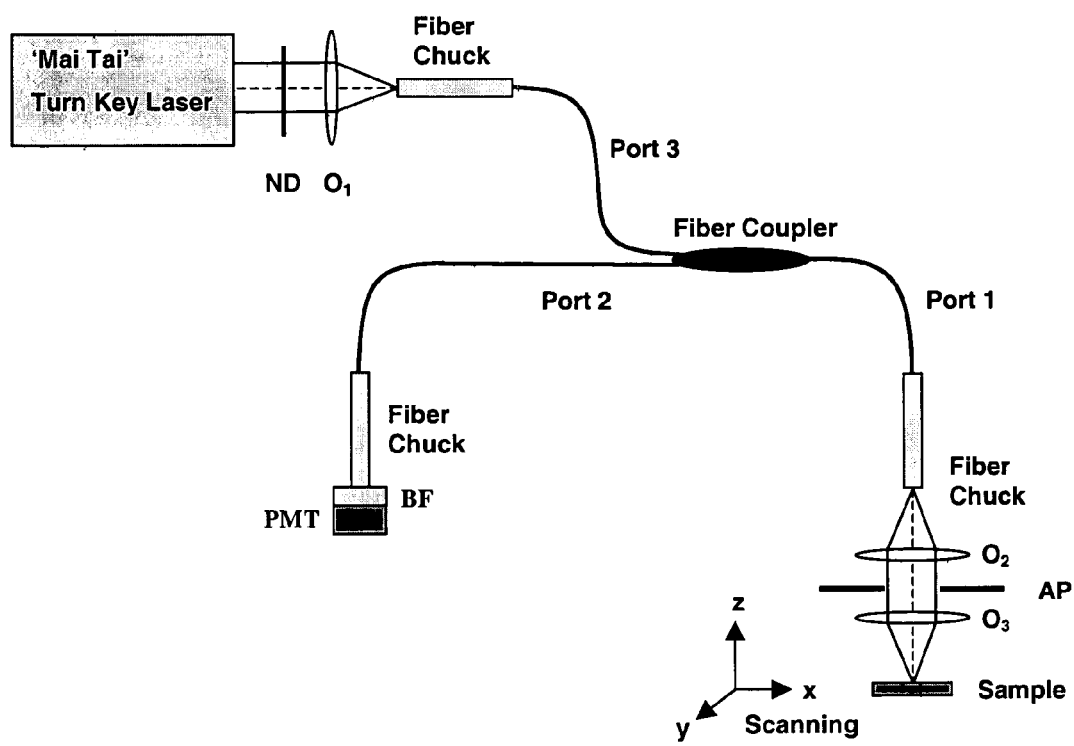
FIG. 1 shows a schematic diagram of a two-photon fluorescence microscope or endoscope according to the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be understood that general reference to microscopes or endoscopes within this specification is also intended to encompass endomicroscopes.

In its simplest form the microscope or endoscope of the invention comprises a source of coherent light suitable to initiate non-linear and preferably two-photon fluorescence in a sample or specimen of interest, which is transmitted from the light source through a first light conductor to a coupler. The light is then directed from the coupler to a second light conductor, the sample end of which is located in the vicinity of the sample region where the sample or specimen is located for imaging. Located in this region the sample end not only transmits coherent light to the sample but is also in position to receive fluoresced light from the sample that is then directed back to the coupler, allowing a proportion of this fluoresced light to be transmitted through a third light conductor to a light detection device located at its terminal.

The nature of the light conductor adopted should be such that it allows contained passage of light therewithin, without substantial loss of power. Preferably the light conductor is comprised of optic fiber, either in the form of single fiber or as a bundle of closely associated fibers. The optic fiber is preferably single-mode optic fiber. For example, the optic fiber used may be of the conventional type, having $GeO_2$ doped cores with pure silica cladding, or of a type having pure silica cores with fluoride doped cladding.

In the case where the light conductors comprise optic fiber the coupler will take the form of a three-port optic fiber coupler, which is preferably also of the single-mode type (at the operational wavelength).

In-fiber Bragg gratings have emerged as a promising solution for dispersion compensation and have received much attention for application in optical communications [11–13]. This technology can be applied to a two-photon fiber optical microscope/endoscope to recompress pulses dispersed by the fiber and fiber coupler. This will allow for a greater two-photon efficiency and therefore increased quantities of two-photon excited fluorescence, leading to an improved signal-to-noise ratio.

So as to allow accurate positioning of the ends of the light conductors the terminals of the first and/or third light conductors and/or the sample end of the second light conductor may have a fiber chuck fitted thereto. These fiber chucks can then be placed in a chuck holder within a positioning device such as an X-Y-Z micro-positioner to allow precise positioning of the fiber tips in each case, so as to achieve the desired function.

The source of coherent light must be suitable to initiate non-linear and preferably two-photon fluorescence in the sample or specimen of interest, which will be located at the sample region for the purpose of imaging. By the phrase "suitable to initiate two-photon fluorescence" it is intended to convey that the coherent light must have a wavelength, pulse width, power and repetition rate that will give rise to two-photon fluorescence in the sample. As will be readily understood two-photon fluorescence involves the illumination of the sample (preferably with coherent light, ie. where waves have a constant phase relationship, preferably in the visible to infra-red wavelength range) and whereby the sample will on absorption of two photons fluoresce by emitting a single higher energy photon.

Preferably the source of coherent light utilised in the present invention is a pulse laser, more preferably a Ti:Sapphire pulse laser. The laser may for example emit coherent light at a wavelength of between about 730 nm to about 870 nm. The pulse width of illumination may for example be within the range of 80 to 120 fs and the repetition rate may for example be within the range of 80 to 82 MHz. Femtosecond, picosecond and continuous wave laser sources may all be used in two-photon fluorescence microscopy.

Ultrashort-pulsed fiber lasers may be used, which demonstrate femtosecond passively mode-locked fiber oscillators by a variety of Kerr-type saturable absorbers. The integration of this highly integrated fiber-based ultra-fast technology to the endoscope system as the primary illumination source provides a cost-effective and even more compact arrangement, through gross reduction of the number of bulk optical components.

To vary power of illumination from the light source it is possible to pass the light through a neutral density filter, rotation of which allows for power variation. The neutral density filter may suitably be located adjacent to the light source. It may also be appropriate to utilise a lens to direct light emitted from the light source or passing through the neutral density filter to the terminal of the first conductor. In the case where the light conductor is or includes optic fiber, the light will preferably be directed to the core of the optic fiber. For example, lenses with numerical aperture (NA) between 0.1 to 0.3 may be adopted for this purpose.

Similarly, it may be appropriate to collimate light emanating from the sample end of the second light conductor, also by utilising a lens, which will be referred to as the first lens. Again, lenses suitable for this purpose may have NA values in the range of 0.1 to 0.3. Preferably the light directed from the first lens will then pass through a variable aperture having a diameter in the range 0.5 to 10 mm. From the variable aperture light is then directed to a second lens. If present this second lens may serve to focus light from the light source onto the sample or specimen of interest, as well as collecting fluoresced light from the sample or specimen that is travelling back towards the aperture, first lens and sample end of the second conductor. The characteristics of the second lens may for example be as follows: NA 0.85–1.2; 40×, 4/170.

Figure 9:
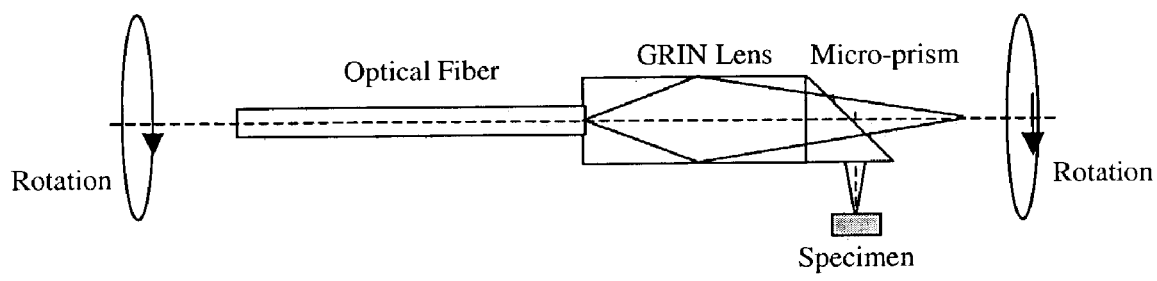
FIG. 9 shows a schematic representation of a rigid rotation scanning geometry that may be achieved in use of the endomicroscope as shown in FIG. 5.

In a further preferred embodiment of the invention the fixed bulk objective lens or lenses and the variable aperture located at the sample end are replaced by a scanning head. The scanning head may comprise a gradient index (GRIN) lens located to receive light from the sample end, and an optical prism which directs light from the gradient index lens transverse to the axis of the gradient index lens. These components will preferably be micro-sized, especially in the case of use within an endomicroscope apparatus. Preferably the optical prism directs light in a substantially perpendicular direction from the axis. The scanning head arrangement will allow freedom of the sample end to be placed and manipulated in vivo. Adoption of the scanning head arrangement, as for example shown in FIG. 5(b) allows the adoption of a rigid rotation scanning geometry, as for example schematically illustrated in FIG. 9. The components of the scanning head are readily commercially available and may be connected by conventional means, such as by using UV curing optical adhesive.

After passing into the second conductor the fluoresced light will return to the coupler and at least a portion of this light will be transmitted to the third conductor, at the terminal of which is located the light detection device. Preferably fluoresced light passing from the terminal to the detection device will first pass through a filter that will substantially prevent passage to the detection device of light other than the fluoresced light. This filter will preferably be a bandpass filter having transmittance in the expected fluorescent light wavelength range. It may be appropriate for the filter to operate at wavelengths within the range of between about 450 nm to about 650 nm, preferably between about 500 nm and about 600 nm, most preferably between about 530 nm and about 570 nm.

While other devices may be utilised to detect the fluoresced light, such as for example photodiodes and split photodiodes, it is preferred that the light detection device comprises a photomultiplier tube. The signal from the photomultiplier tube (PMT) may then be manipulated in a conventional manner to produce an image of the sample. This may be achieved by scaling the relative PMT voltage in a suitable range (0 to 10 V, for example) and using a 256 bit greyscale colour map to digitally reconstruct images. In this way an analogue signal of 0V corresponds to digital bit 0 (black) and 10V corresponds to digital bit 255 (white). All other values of the PMT voltage in this range are scaled over the remaining bits, i.e. 10/254 represents 0.03937007V per bit.

In preferred embodiments of the invention lenses, filters and the terminals of the light conductors will be located within protective housings. In particular it is preferred for the sample end of the second conductor and the optional first and/or second lenses and aperture to be located within a protective housing. This is of course especially important in the case where the apparatus of the invention is being utilised as an endoscope or endomicroscope. Also in the case of endoscopic use it may be appropriate for a camera such as a video or digital camera to be provided at or about the sample region, along with a light source (which will preferably be configured to avoid interference with endoscopic imaging) to assist in directing the sample region to the desired location within the patient's body. It may also be appropriate for a suction mechanism to be provided for drawing the sample into the sample region. Similarly, a heating device may be incorporated within at least those components of the apparatus that will be internal during endoscopic use, to assist with patient comfort and ensure optimal operation of the equipment. It is also preferred for components of the apparatus that will be internalised during endoscopy to be provided with a soft covering, coating or laminate to both protect the equipment from exposure to potentially damaging acids, alkali, enzymes and the like within bodily fluids and to minimise discomfort to the patient and/or damage or disruption to organs and tissues. It is also preferred that the covering, coating or laminate is of a form that can readily be lubricated and sterilised, by conventional means.

The two-photon fluorescence microscope/endoscope of the present invention can be configured to incorporate other imaging modalities. For example, the present invention may be combined with optical coherence tomography and/or sonohysterography equipment, which would offer the capability for real time acquisition of detailed sample information that would ordinarily require two separate processes.

It is also possible to incorporate in conjunction with the scanner head of the invention a micropositioning functionality which will serve to allow controlled location of the scanning head in vivo. The features that will allow this positioning capability are well known in conventional endoscopic apparatus.

The present invention will now be described further, by way of example only, with reference to the following non-limiting examples:

EXAMPLE 1

Arrangement of Two-photon Fluorescence Microscope

The arrangement of a two-photon fluorescence microscope is given in FIG. 1. Ultrashort optical pulses generated from a turn-key Ti:Sapphire laser (Spectra Physics, Mai Tai) of a wavelength range from 730 nm to 870 nm, pulse width 80 fs and repetition rate 80 MHz were used as the illumination. This laser beam was coupled into a port (port 3) of a three-port single-mode fiber coupler via a 0.25 NA objective $O_1$. Rotation of a neutral density filter, ND, placed before the objective $O_1$ allowed variation of the input power. The output beam from port 1 of the coupler was collimated by a 0.25 NA objective $O_2$ and then passed through a variable aperture, AP, to fill the back aperture of the imaging objective $O_3$ (0.85 NA, 40×, 4/170). The emitted fluorescence from a sample was collected by the objective $O_3$ and returned via the same optical path used for pulse delivery. The signal was delivered via port 2 of the coupler into a photomultiplier tube. A bandpass filter, BF, operating at wavelength 550 nm (±20 nm) was placed in the beam path to ensure that only the fluorescence signal was detected.

Each port of the fiber coupler was placed in a chuck holder in an X-Y-Z micro-positioner to allow precise positioning of the fiber tip at the focus of an objective.

To obtain the optimum delivery of the pulsed laser beam a fiber coupler (Newport) was used that was designed for operation at wavelength 785 nm with an equal splitting ratio. The length of each arm of the coupler was 1 m. The measured coupling efficiency from ports 2 and 3 to port 1 varied between 20%–38% in the wavelength range between 770 nm to 870 nm. This property implies that the laser power of up to 80 mW–150 mW in this wavelength can be delivered to a microscope objective. As most commercial objectives have a transmittance of approximately 50% to 60% in the infrared region and the ultrashort pulsed beam is broadened approximately to a few picoseconds after it transmits through the coupler, this coupler is capable of delivering a laser beam of sufficient power for two-photon excitation.

The optical fiber used is of a single mode type (at the operating wavelength) and has a core/cladding ratio of approximately 5/125 and a NA of 0.11. The operating wavelength of this coupler is 785 nm.

EXAMPLE 2

Assessment of Coupling Efficiency

In the visible range in which two-photon fluorescence falls, the coupling efficiency of this coupler (from the apparatus exemplified in Example 1) may be reduced and an equal splitting ratio between ports 2 and 3 may not necessarily be maintained. To confirm these features, the mode profile and coupling efficiency at ports 2 and 3 were measured while port 1 was illuminated by a continuous wave beam at wavelength 532 nm (Spectra Physics, Millenia). It was found that the field distribution from ports 2 and 3 is a single-mode profile, which is consistent with the estimation based on the core size and numerical aperture of the coupler in the visible range. The coupling efficiency at port 2 was approximately 1% with a splitting ratio of 90:10 between ports 2 and 3. As a result, using port 2 for the signal collection of two-photon fluorescence and port 3 for delivery of the pulsed beam means that the coupler acts as a low-pass filter and that the strength of two-photon fluorescence signal can be maximised.

EXAMPLE 3

Depth Discrimination Characterisation

Figure 2:
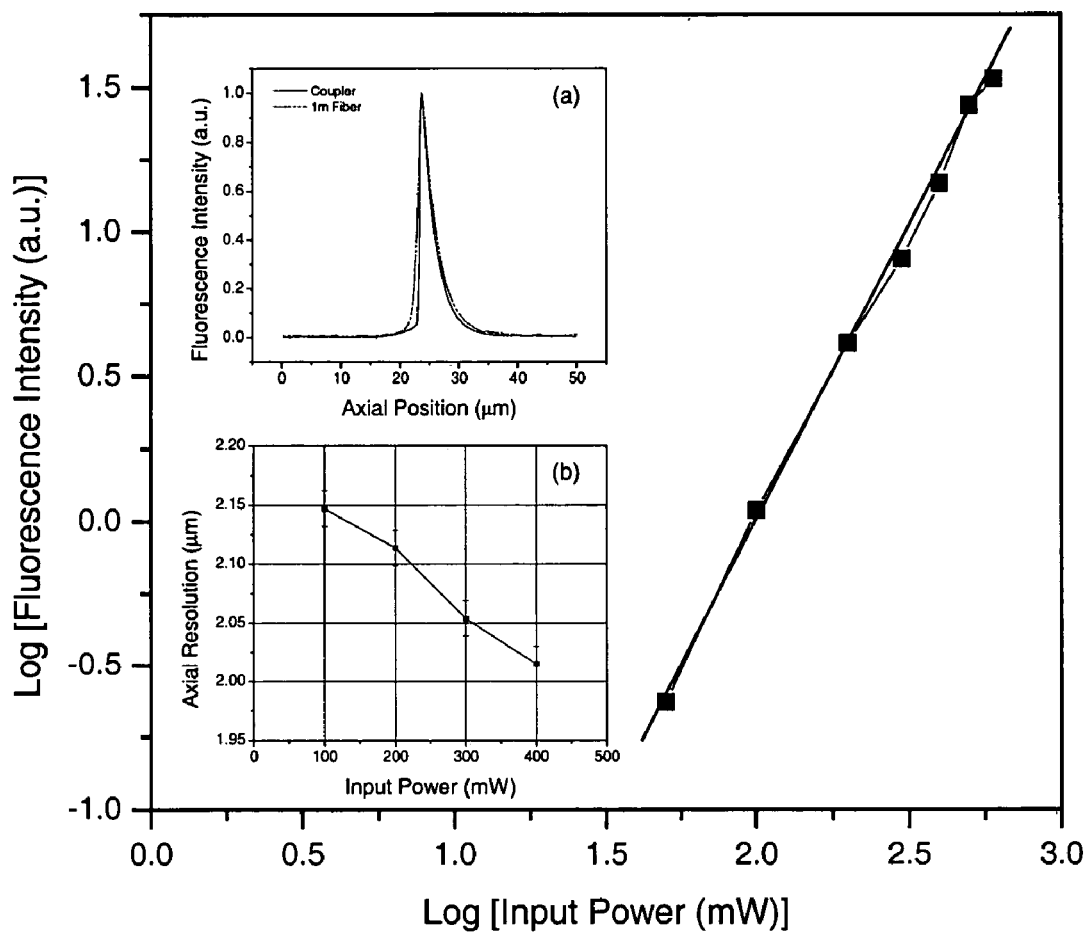
FIG. 2 shows a plot of two-photon excitation efficiency of the microscope or endoscope shown in FIG. 1 showing the log of fluorescence intensity (a.u.) on the Y axis verses the log of input power (mW) on the X axis. Insert (a) shows axial responses to a thin fluorescent layer in the system using a coupler (solid) or a large-area detector without a pin hole (dashed) and insert (b) shows the dependence of the width of the axial response on the excitation power.

The depth discrimination of the new imaging system (as demonstrated in FIG. 1) was characterised by measuring the axial response to a thin fluorescent layer. The layer was produced on a cover slide by placing a few fluorescent drops comprising AF-50 dye dissolved in isopropanol until they were dried. The sample was excited by two-photon absorption at a wavelength of 800 nm. The measured fluorescence intensity as a function of the power input to port 3 of the coupler is shown in FIG. 2 in a log-log scale. It can be seen that the gradient of the curve is approximately 2.0±0.1 indicating that the fluorescence signal varies with the square of the input power, as expected for two-photon excitation.

EXAMPLE 4

Assessment of Axial Response

Typical axial responses obtained using the apparatus shown in FIG. 1 are shown in inset (a) of FIG. 2. It is shown that the full width at half maximum (FWHM) of the axial response (solid curve in FIG. 2a) measured in the new two-photon fluorescence microscope, $\Delta z$, is approximately 2.1 µm, which is reduced by 30% compared with that measured by a large area detector without a pinhole[6] (solid curve in FIG. 2a). The decrease in the FWHM indicates the enhancement of the optical sectioning effect and therefore the improvement in axial resolution. In this case, the resolution improvement results from the aperture of port 1, which acts as an effective confocal aperture. In inset (b) of FIG. 2, the dependence of the FWHM $\Delta z$ on the incident power to port 3 is depicted, showing that the resolution is improved as the input power is increased. This feature is caused by the fact that the spectrum of the pulsed beam is broadened and blue-shifted due to self-phase modulation and self-steepening, respectively, in a fiber.

EXAMPLE 5

Three-dimensional Imaging

Figure 3:
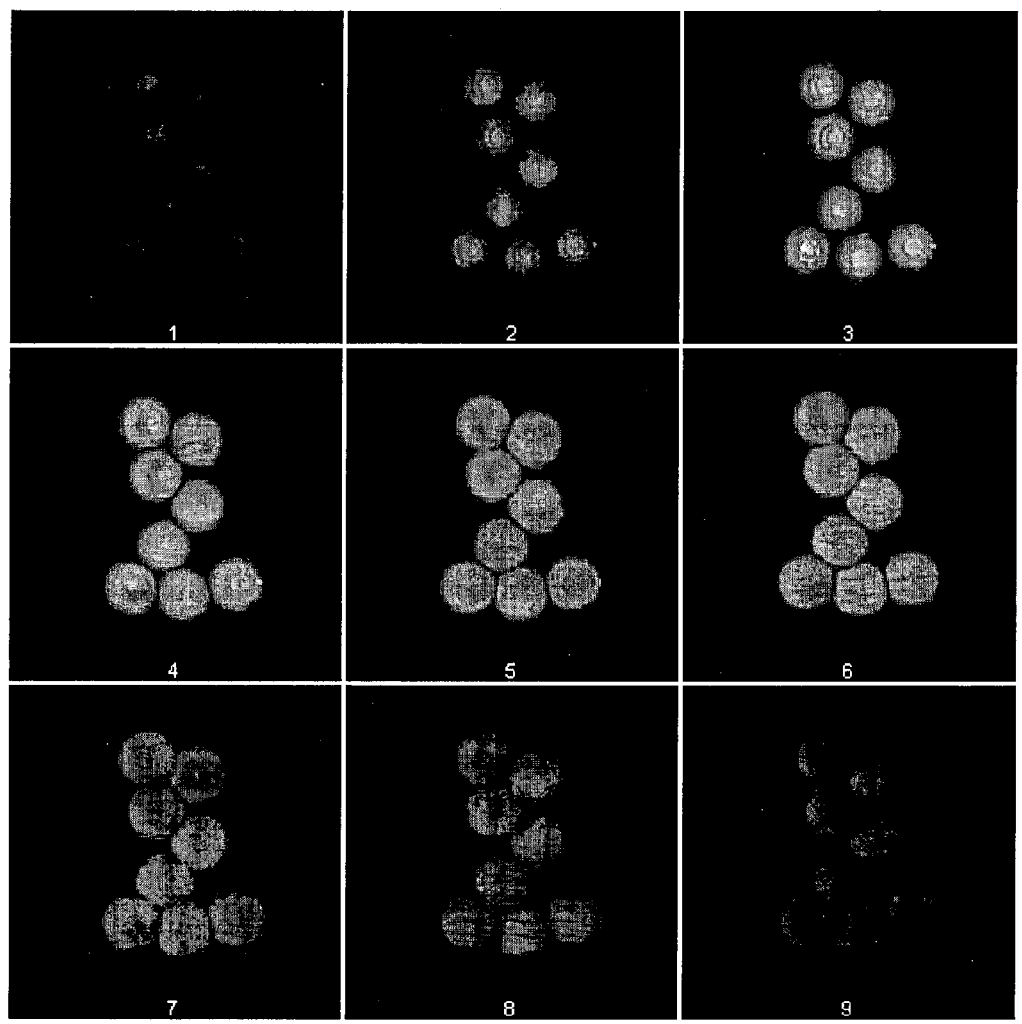
FIG. 3 shows images of 10 µm diameter fluorescent polymer microspheres obtained using the two-photon fluorescence microscope or endoscope as shown in FIG. 1. The size of slices is 60 µm×60 µm and the slice spacing is 1 µm. The excitation power adopted was 8 mW at the focus.
Figure 4:
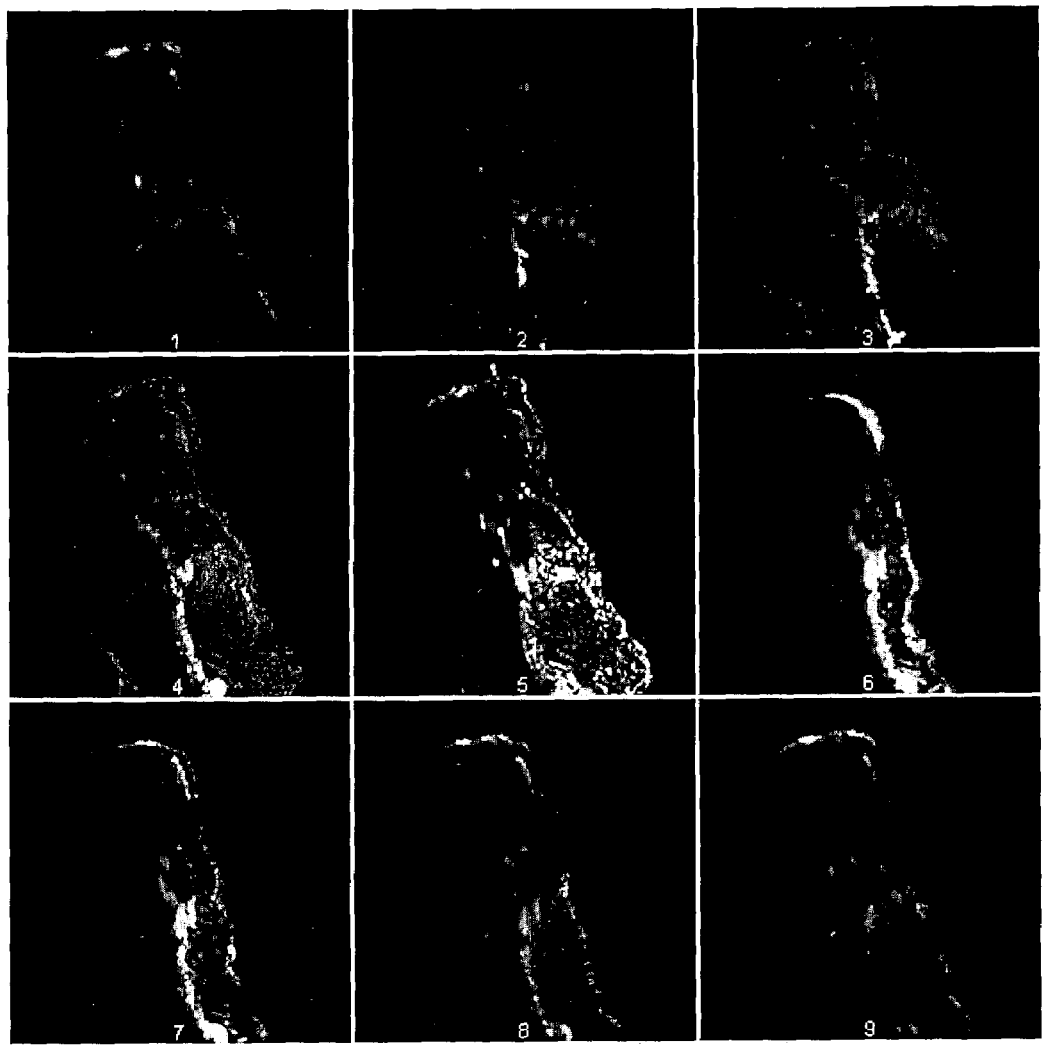
FIG. 4 shows images of *Griffithsia* sea algae obtained using a two-photon fluorescence microscope or endoscope as shown in FIG. 1. The size of slices is 150 µm×150 µm and the slice spacing is 1µm. The excitation power adopted was 8 mW at the focus.

To demonstrate the three-dimensional imaging capability of the system (as shown in FIG. 1), FIG. 3 shows a series of image sections taken at 1 µm depth step into an ensemble of 10 µm fluorescent polymer microspheres. FIG. 4 displays a series of image sections of the autofluorescence signal from sea algae, *Griffithsia,* demonstrating the applicability of the instrument for biological study. Both image sets exhibit high contrast and the pronounced optical sectioning property of the system.

EXAMPLE 6

Inclusion of Scanning Head in Two-photon Endomicroscope

Figure 5:
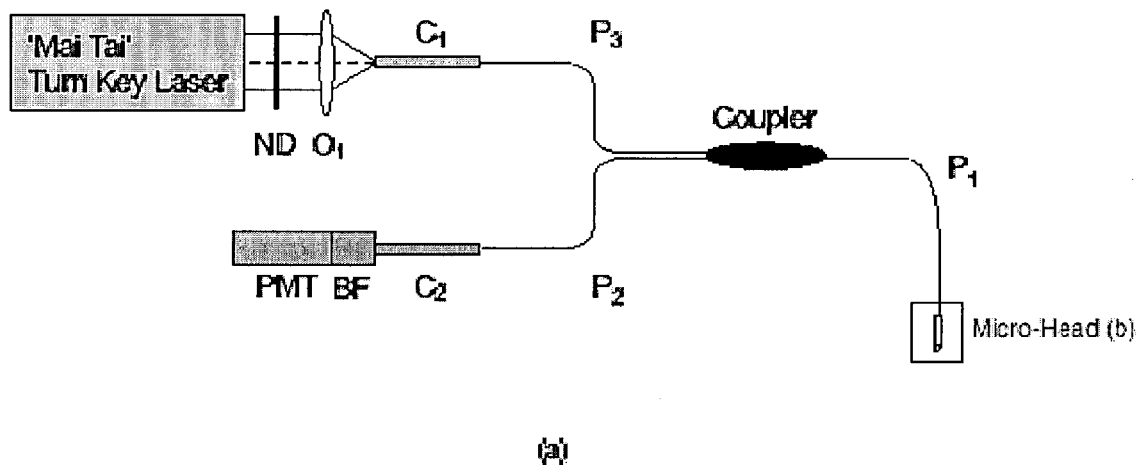
FIG. 5(*a*) shows a schematic diagram of a two-photon fluorescence endomicroscope of the invention using a single-mode optical fiber coupler. $O_1$:0.25 NA 10×microscope objective, ND:Neutral density filter; BF:Bandpass filter; $C_1,C_2$:Fiber chucks, $P_1,P_2,P_3$:Coupler ports and FIG. 5(*b*) shows an enlargement of the scanning head.
Figure 5:
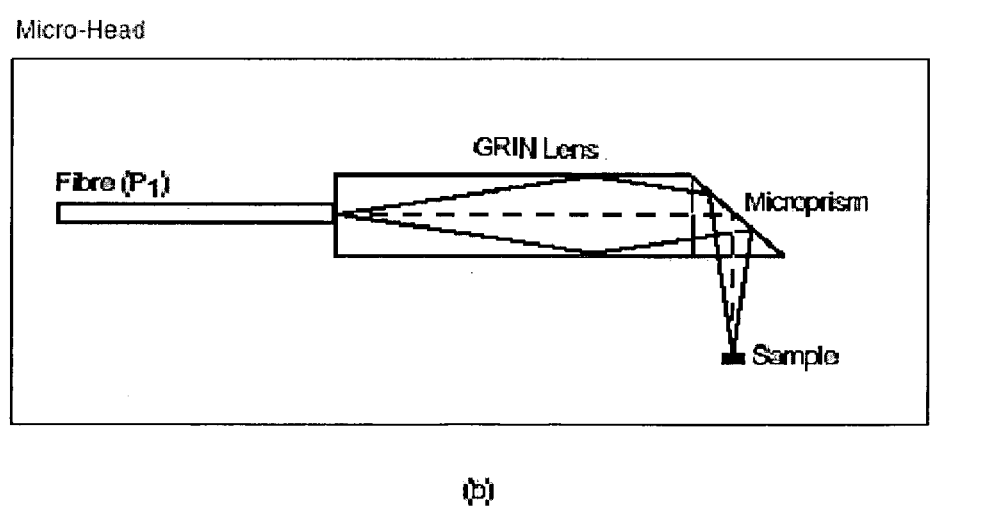

FIG. 5 shows a schematic representation of a two-photon endomicroscope, in all other respects the same as that shown in FIG. 1, which includes a scanning head (also referred to as a micro-scanning head) in place of the fixed objective/s and variable aperture at the sample end. The scanning head essentially comprises miniature beam focusing and directing optics. The single-mode optical fiber that is port 1 of the fiber coupler is attached to a 1 mm diameter Plano-Plano, 0.25 pitch, 0.46 NA GRIN lens (Newport: LG1830-2) designed for operation at a wavelength of 830 nm. The pitch of the lens was chosen to yield the required Gaussian beam parameters. A 0.5 mm BK7 right angle microprism (Edmund Industrial Optics: A45-946) is mounted at the distal end of the GRIN lens to direct the beam perpendicular to the axis of the endoscope. In other experiments a 1.0 mm BK7 right angle microprism has been used. The microprism, GRIN lens and optical fiber were all attached with ultraviolet curing optical adhesive (Norland) to form a single unit, which has an approximate working distance of 2.0 mm.

EXAMPLE 7

Coupling Efficiency of Endomicroscope That Includes Scanning Head

Figure 6:
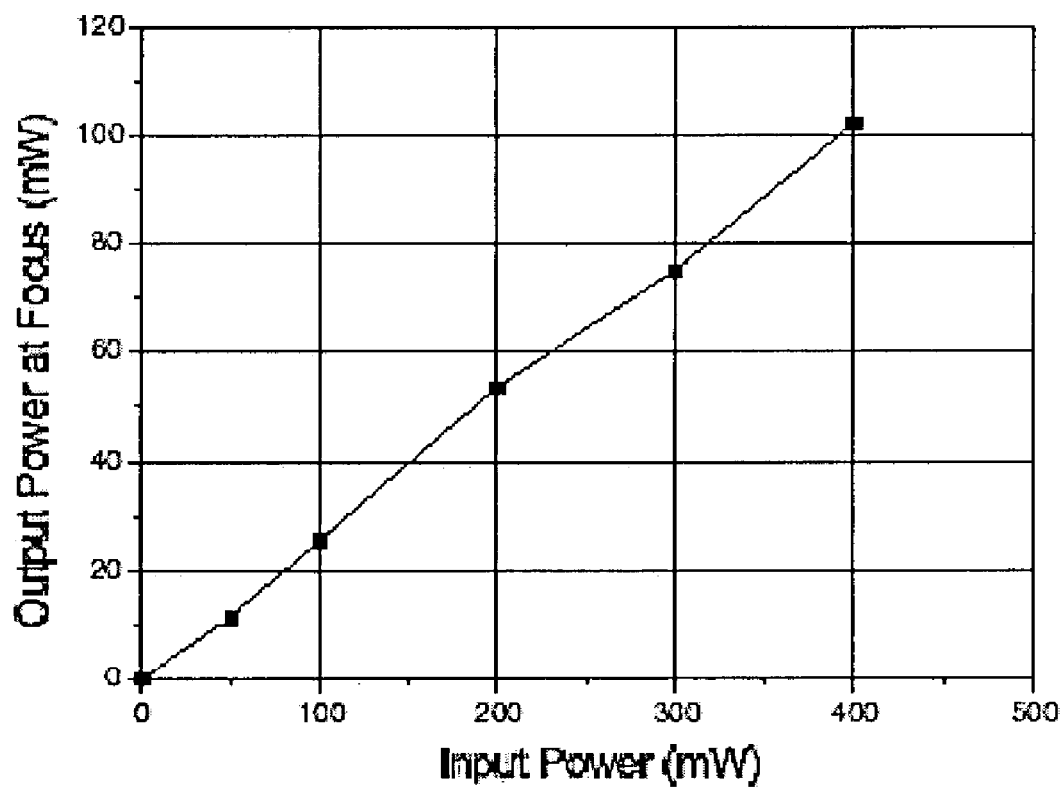
FIG. 6 shows a plot of output power at focus (mW) against input power (mW) measured at port 3 of the coupler, which demonstrates coupling efficiency of the endomicroscope as shown in FIG. 5.

Using the arrangement shown in FIG. 5 and with the scanning head attached to port 1 of the fiber coupler, the coupling efficiency for illumination of wavelength 800 nm was measured to determine the magnitude of power that can be delivered to a sample. The results are shown in FIG. 6, which depicts the measured output power at the focus as a function of input power to port 3 of the coupler. For illumination of wavelength 800 nm, the coupling efficiency of the system including the micro-head is reduced to approximately 28% compared with approximately 35% obtained with the system using bulk imaging components. This decrease arises for a number of reasons, including the slight mismatch in the refractive indices of the fiber core, GRIN lens, microprism and the optical adhesive. Furthermore, if one considers the geometry of the arrangement shown in FIG. 5 it can be seen that a certain fraction of the incident beam will be transmitted through the microprism along the principal axis and will therefore be lost. This fraction was measured and found to be approximately 5–8% of the power input to port 3.

EXAMPLE 8

Axial Response of Endomicroscope That Includes Scanning Head

Scanning using the arrangement shown in FIG. 5 may be achieved by using the input fiber (i.e. port 1 of the coupler in this case) in conjunction with an optical coupling element (fiber ferrule) to couple the incident illumination across a small air gap to a second single-mode fiber with the micro-optic assembly attached. In this way it is possible to scan (rotate) the beam in a circumferential manner to image cross sectionally through a biological structure into which it was inserted. However, to demonstrate the feasibility of the design for use in fiber-optic TPFM, a rotational scan was not performed. Rather, the axial response in two cases was investigated.

Figure 7:
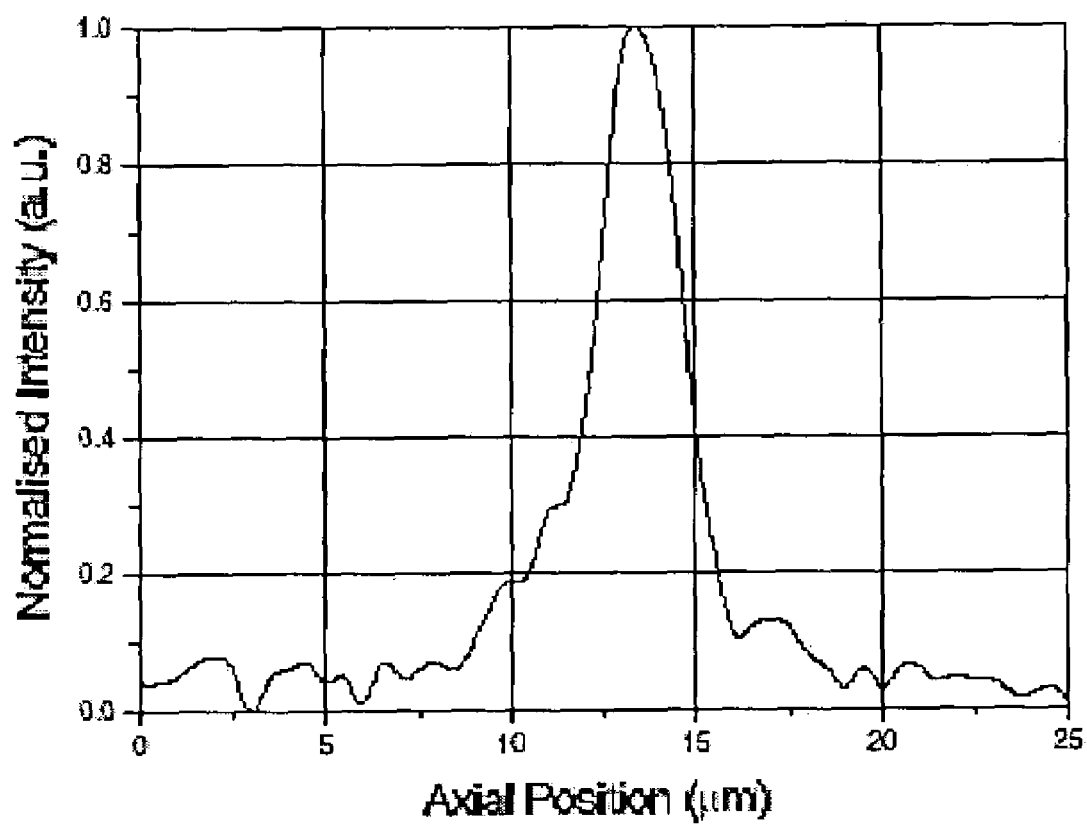
FIG. 7 shows a plot of normalised intensity (a.u.) against axial position (:m) obtained using the endomicroscope shown in FIG. 5, which demonstrates axial response to a plane mirror.

First, the response to a plane mirror was measured by continuous scanning through focus in the z-direction. Second, the mirror was replaced with a fluorescent polymer block to measure the axial fluorescence response using the same scanning method. These two axial responses give measures of axial resolution of the endoscope in the case of non-fluorescence and two-photon fluorescence imaging. The measured response for the reflection (ie. mirror) case is shown in FIG. 7. Here, the optical sectioning ability of the instrument with the micro-head assembly attached is clearly demonstrated through the FWHM of the response curve, which is approximately 2.8 µm.

Figure 8:
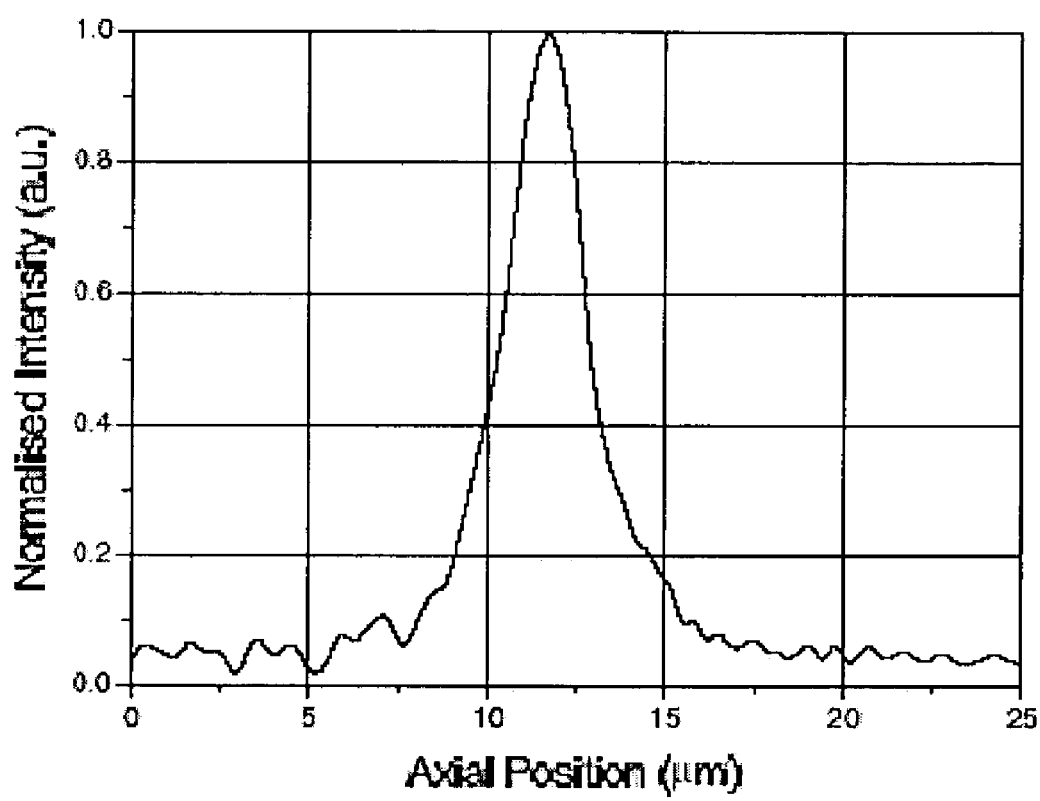
FIG. 8 shows a plot of normalised intensity (a.u.) against axial position (:m) obtained using the endomicroscope shown in FIG. 5, which demonstrates axial response to a polymer sample.

The practicability of the instrument for use in biological studies is reliant on the ability of the micro-head to collect two-photon excited fluorescence from a sample. FIG. 8 demonstrates this ability and depicts the axial response of a planar fluorescent polymer sample obtained by coupling 400 mW of 800 nm laser illumination to port 3 of the fiber coupler. The FWHM of the response curve is approximately 2.6 µm, which indicates a good optical sectioning ability. It should be pointed out that the measured axial resolution of the fiber coupler based system for an input power of 400 mW was approximately 2.0 µm. One reason for the decrease in the optical sectioning performance of the system using the micro-head is due to the lower NA of the GRIN lens compared to the NA of the bulk imaging objective used in earlier experiments.

EXAMPLE 9

Simulation of Internal Imaging

Figure 10:
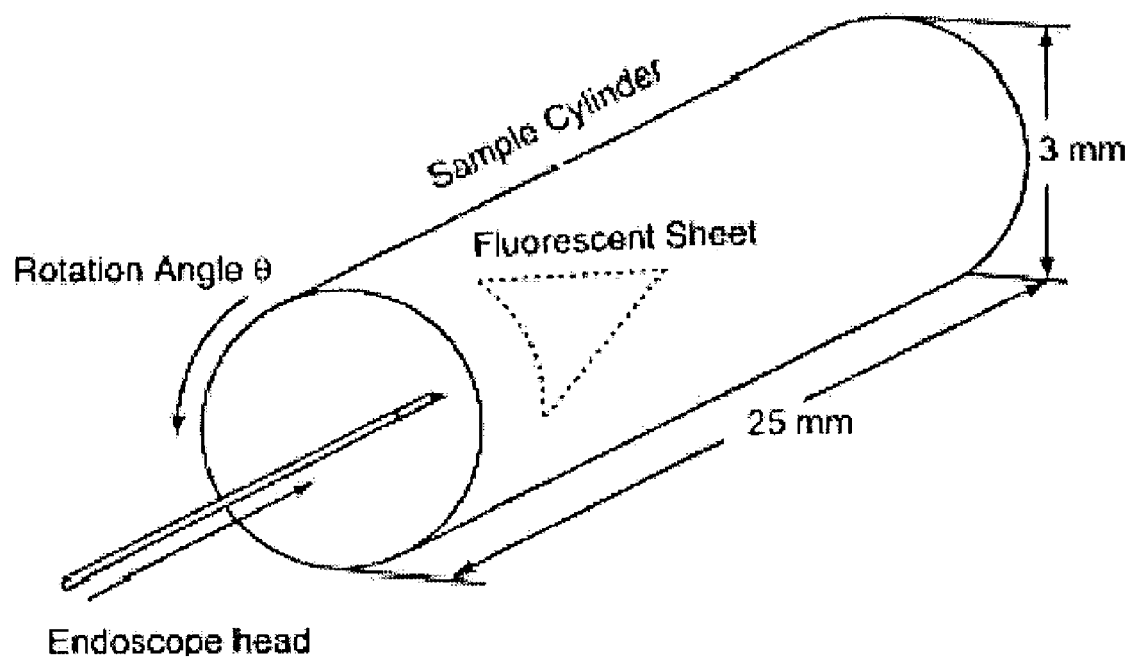
FIG. 10 Schematic diagram of the cylindrical sample holder used in Example 9.
Figure 11:
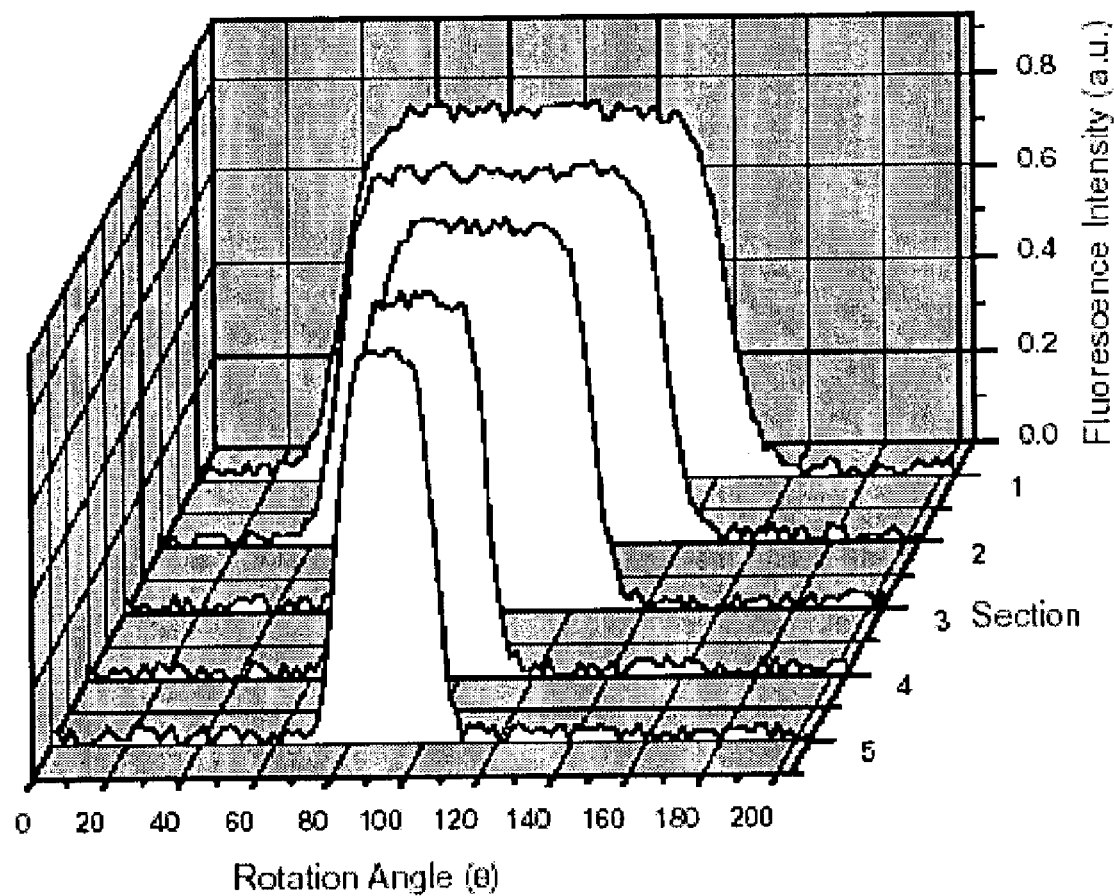
FIG. 11 Plot of rotation angle (θ) against fluorescence intensity (a.u.) for a series of transverse cross-sectional images taken at 0.5 mm steps into a cylindrical channel having a 5 mm equilateral triangle fluorescent sheet attached to the internal surface. The initial series (No. 1) was acquired 1.0 mm into the cylinder relative to the base of the fluorescent triangle.

To demonstrate the feasibility of the micro-endoscope head for imaging an internal structure, rotating of the distal optics inside an internal body cavity was simulated by rotating a hollowed cylindrical sample holder around a fixed micro-endoscope head. The sample holder as shown in FIG. 10 was machined from a 25 mm length of Perspex to form a hollowed cylindrical rod of 3 mm inner diameter and mounted to the shaft of a variable speed 12V DC rotary motor. The speed of rotation could be accurately controlled by the potential supplied to the motor. A two-dimensional image was constructed by progressively increasing the insertion depth of the micro-endoscope head into the cylinder with a step size of 0.5 mm and performing a single rotational scan. The sample consisted of a fluorescent paper sheet cut into the shape of a 5.0 mm equilateral triangle. The sheet was prepared by uniformly coating a piece of 75 g/m2 paper with a mixture of AF-50 fluorescent dye and isopropyl alcohol.[4] Double-sided adhesive tape was used to secure the sample inside the cylinder oriented such that the base of the triangle was parallel with the circumference of the cylinder.

FIG. 4 shows five acquisitions into the cylinder. The first series is obtained by rotating the cylinder with the focus of the micro-endoscope positioned 1.0 mm along the fluorescent sample. The trigonometric shape of the top constructed by the five curves reveals that the region of the detected fluorescence intensity as a function of the angular displacement of the cylindrical sample holder is consistent with the actual shape of the fluorescent material. It is clearly shown that as the micro-endoscope head is inserted further into the cavity, the rotation angle range over which fluorescence is detected decreases accordingly.

References
1. W. Denk, J. H. Strickler and W. W. Webb, *Science,* 248, 7 (1990).
2. T. Dabbs and M. Glass, *Appl. Opt.,* 31, 705 (1992)
3. J. Benschop and G. van Rosmalen, *Appl. Opt.* 30, 1179 (1991).
4. S. Kimura and T. Wilson, *Appl. Opt.,* 30, 2143 (1991).
5. M. Gu, C. J. R. Sheppard and X. Gan, *J. Opt. Soc. Am.* A, 8, 1755 (1991).
6. D. Bird and M. Gu, "Resolution improvement in two-photon fluorescence microscopy using a single-mode fiber", *Appl. Opt.* 41, 1852 (2002).
7. M. V. Iravani, *Electron. Lett.* 22, 103 (1986).
8. Y. Fujii and Y. Yamazaki, *J. Microscopy,* 158, 145 (1989).
9. H. Zhou, M. Gu and C. J. R. Sheppard, *Optik* 103, 45 (1996).
10. G. J. Tearney, S. A. Boppart, B. E. Bouma, M. E. Brezinski, N. J. Weissman, J. F. Southern and J. G. Fujimoto, "Scanning single-mode fiber optic catheter-endoscope for optical coherence tomography", *Opt. Lett.,* 21, 543–545 (1996).
11. F. Ouellette, "All-fiber filter for efficient dispersion compensation", *Opt. Lett.,* 16, 303 (1991).
12. B. J. Eggleton, P. A. Krug and L. Poladian, "Experimental demonstration of compression of dispersed optical pulses by reflection from self-chirped optical fiber Bragg gratings", *Opt. Lett.,* 19, 877 (1994).

13. M. E. Fermann, K. Sugden and I. Bennion, "Environmentally stable high-power soliton fiber lasers that use chirped fiber Bragg gratings", *Opt. Lett.*, 20, 1625 (1995).
14. D. Bird and M. Gu, Opt. Lett., 27, 1031 (2002).

The claims defining the invention are as follows:

1. A two-photon fluorescence endoscope comprising:
   (a) an ultrashort pulsed laser source of coherent light suitable to initiate two-photon fluorescence in a sample of interest located at a sample region;
   (b) a first single mode fiber optic light conductor positioned to receive at its terminal light from said light source and direct said light to a three-port single mode fiber coupler;
   (c) a second single mode fiber optic light conductor having at its sample end a scanning head comprising a gradient index lens located to receive light from said sample end, and an optical prism which directs light from said gradient index lens transverse to axis of said gradient index lens, the second conductor located to receive light introduced to said coupler from said first conductor and direct said light to said sample via said sample end, said sample end also located to receive fluoresced light from said sample that is collected by said optical prism, passes through said index gradient lens and is thereby directed to said sample end such that said second conductor may direct said fluoresced light to said coupler;
   (d) a third single mode fiber optic light conductor located to direct fluoresced light from said coupler to a light detection device via a terminal of said third light conductor.

2. The endoscope according to claim 1 wherein a neutral density filter is provided, rotation of which allows power variation of said coherent light.

3. The endoscope according to claim 1 wherein a lens is provided to direct coherent light from said source to said terminal of said first conductor.

4. The endoscope according to claim 1 wherein a fiber chuck is located at said terminal of said first light conductor.

5. The endoscope according to claim 4 wherein position of said fiber chuck located at said terminal of said first light conductor is controlled by a positioning device.

6. The endoscope according to claim 1 wherein said gradient index lens, said optical prism and said sample end are contained within a protective housing.

7. The endoscope according to claim 1 wherein a filter is provided between said detection device and said terminal of said third light conductor which substantially prevents passage to said detection device of light other than said fluoresced light.

8. The endoscope according to claim 7 wherein said filter is a bandpass filter.

9. The endoscope according to claim 1 wherein a fiber chuck is located at said terminal of said third light conductor.

10. The endoscope according to claim 9 wherein position of said fiber chuck located at said terminal of said third light conductor is controlled by a positioning device.

11. The endoscope according to claim 1 wherein said detection device is a photomultiplier tube.

12. The endoscope according to claim 1 wherein the laser is a Ti:Sapphire laser.

13. The endoscope according to claim 1 wherein said coherent light is at a wavelength of between about 730 nm to about 870 nm.

14. The endoscope according to claim 1 provided with a suction mechanism for drawing said sample into said sample region.

15. The endoscope according to claim 1 provided with a camera and light source to assist in directing said sample region to a desired location.

16. The endoscope according to claim 1 comprising a heater for heating some or all components of the endoscope located internally during use.

17. A two-photon fluorescence endoscope comprising:
   (a) an ultrashort pulsed laser suitable to initiate two-photon fluorescence in a sample of interest to be located at a sample region;
   (b) a first single mode fiber optic light conductor having at its terminal a fiber chuck under positional control of a positioning device, wherein light from said source passes through a neutral density filter and a lens which directs the light to the terminal of the first conductor, which in turn directs said light to a three-port single mode fiber coupler;
   (c) a second single mode fiber optic light conductor having at its sample end a scanning head comprising a gradient index lens located to receive light from said sample end, and an optical prism which directs light from said gradient index lens transverse to axis of said gradient index lens, the second conductor located to receive light from said first conductor and direct light to said sample via the sample end, said sample end also located to receive fluoresced light from said sample that is collected by said optical prism, passes through said gradient index lens and is thereby directed to said sample end such that said second conductor may direct said fluoresced light to said coupler;
   (d) a third single mode fiber optic light conductor having at its terminal a fiber chuck under positional control of a positioning device, the third conductor located to direct light from said coupler to a photomultiplier tube light detection device via said terminal of said third conductor and a bandwidth filter that substantially prevents passage to said detection device of light other than said fluoresced light.

* * * * *